(12) United States Patent
Schuessler

(10) Patent No.: US 11,433,001 B2
(45) Date of Patent: *Sep. 6, 2022

(54) SYSTEM, APPARATUS AND METHOD EMPLOYED WITH ENTERAL SYSTEMS

(71) Applicant: KPR U.S., LLC, Mansfield, MA (US)

(72) Inventor: Wayne Schuessler, St. Louis, MO (US)

(73) Assignee: KPR U.S., LLC, Mansfield, MA (US)

( * ) Notice: Subject to any disclaimer, the term of this patent is extended or adjusted under 35 U.S.C. 154(b) by 3 days.

This patent is subject to a terminal disclaimer.

(21) Appl. No.: 16/456,502

(22) Filed: Jun. 28, 2019

(65) Prior Publication Data

US 2019/0321265 A1  Oct. 24, 2019

Related U.S. Application Data

(63) Continuation of application No. 14/576,905, filed on Dec. 19, 2014, now Pat. No. 10,532,007.

(51) Int. Cl.
*A61J 15/00* (2006.01)
*A61M 39/10* (2006.01)
(Continued)

(52) U.S. Cl.
CPC ........... *A61J 15/0096* (2013.01); *A61J 15/00* (2013.01); *A61J 15/0092* (2013.01);
(Continued)

(58) Field of Classification Search
CPC ...... A61J 15/00; A61J 15/003; A61J 15/0026; A61J 15/0073; A61J 15/0092; A61J 15/0096

See application file for complete search history.

(56) References Cited

U.S. PATENT DOCUMENTS 4,707,906 A  11/1987 Posey et al.
4,735,607 A   4/1988 Keith, Jr.
(Continued)

FOREIGN PATENT DOCUMENTS

EP     2253350 A1   11/2010
WO     9217150 A1   10/1992
WO  2010029853 A1    3/2010

OTHER PUBLICATIONS

Alternate Syringes: Low Displacement Option, Rork Swisher, ISO 80369 Series Meeting, Berlin, Germany, Mar. 19, 2014, 11 pages.
(Continued)

*Primary Examiner* — Kevin C Sirmons
*Assistant Examiner* — Leah J Swanson
(74) *Attorney, Agent, or Firm* — ArentFox Schiff LLP

(57) ABSTRACT

A connector system is configured to fluidly connect a nasogastric tube assembly including a lumen and a tube to a medical device. The system includes a connector including: a fitting configured to provide a fluid-tight connection with the medical device; a neck coupled to the fitting, the neck configured to attach to the nasogastric tube assembly; and a body coupled to the neck, the body configured to provide a fluid-tight connection with the nasogastric tube assembly when at least partially inserted within the lumen; and a first tether including a first fastening region defining a first opening configured to receive the neck, a second fastening region defining a second opening configured to couple to the nasogastric tube assembly, and a link coupling the first fastening region to the second fastening region, the link configured to maintain a fixed distance separating the first fastening region from the second fastening region.

15 Claims, 6 Drawing Sheets

(51) Int. Cl.
 *A61M 39/12* (2006.01)
 *A61M 39/20* (2006.01)
 *A61M 5/14* (2006.01)
 *F16L 15/04* (2006.01)
 *F16L 15/08* (2006.01)
 *F16L 21/08* (2006.01)

(52) U.S. Cl.
 CPC .......... *A61M 5/1418* (2013.01); *A61M 39/10* (2013.01); *A61M 39/12* (2013.01); *A61M 39/20* (2013.01); *F16L 15/04* (2013.01); *F16L 15/08* (2013.01); *F16L 21/08* (2013.01); *A61M 2039/1027* (2013.01); *A61M 2039/1033* (2013.01); *A61M 2039/1077* (2013.01)

(56) References Cited

U.S. PATENT DOCUMENTS

| | | | |
|---|---|---|---|
| 5,079,802 A | 1/1992 | Blase et al. | |
| 5,309,604 A | 5/1994 | Poulsen | |
| 5,413,561 A | 5/1995 | Fischell et al. | |
| 5,507,460 A | 4/1996 | Schneider | |
| 6,158,095 A | 12/2000 | Lassiter | |
| 6,367,118 B1 | 4/2002 | Berfield | |
| D468,015 S | 12/2002 | Horppu | |
| 6,609,520 B1 | 8/2003 | Carlsen et al. | |
| D492,030 S | 6/2004 | Rani | |
| 7,166,088 B2 | 1/2007 | Heuser | |
| D629,099 S | 12/2010 | Kilani | |
| 7,850,669 B1 | 12/2010 | Moore et al. | |
| 7,882,600 B2 * | 2/2011 | Judd | H02G 11/02 24/339 |
| D634,007 S | 3/2011 | Zinger et al. | |
| 8,177,736 B2 * | 5/2012 | Kopperschmidt | A61M 1/3656 604/4.01 |
| 8,333,745 B2 * | 12/2012 | Tully | A61F 5/4404 248/229.16 |
| 8,361,040 B2 * | 1/2013 | Spohn | A61M 5/14546 604/174 |
| D709,753 S | 7/2014 | Guala | |
| 2008/0140020 A1 | 6/2008 | Shirley | |
| 2008/0183153 A1 | 7/2008 | Enns | |
| 2012/0191037 A1 | 7/2012 | Patel et al. | |
| 2013/0086773 A1 | 4/2013 | Cude | |
| 2013/0270819 A1 | 10/2013 | Amborn et al. | |
| 2014/0073853 A1 * | 3/2014 | Swisher | A61B 1/051 600/104 |
| 2014/0243625 A1 * | 8/2014 | Warren | A61B 5/1459 600/310 |
| 2016/0067471 A1 | 3/2016 | Ingram et al. | |
| 2016/0143815 A1 * | 5/2016 | Koelper | A61M 39/10 604/533 |

OTHER PUBLICATIONS

Examination Report for European Patent Application No. 15823271.0, dated Apr. 13, 2018, 3 pages.
International Search Report and Written Opinion for Application No. PCT/US2015/066285, dated Mar. 2, 2016, 10 pages.

* cited by examiner

SYSTEM, APPARATUS AND METHOD EMPLOYED WITH ENTERAL SYSTEMS

CROSS-REFERENCE TO RELATED APPLICATION

This application is a continuation of U.S. application Ser. No. 14/576,905, filed Dec. 19, 2014, the entire content of which is incorporated herein by reference.

BACKGROUND

1. Technical Field

The present disclosure relates generally to enteral systems, and more particularly, systems, apparatus and methods employed with enteral systems to permit both administration and removal of fluids via an enteral tube.

2. Background of Related Art

Enteral systems often employ a nasogastric tube for suction of gastric contents, decompression, irrigation, medication delivery and the delivery of radiological contrast material, as some examples. Once in place, the same tubing is sometimes also used for feeding. Generally, the tube includes a main lumen and a vent lumen where the main lumen is used for the respective suction and feeding operations. The vent lumen is used to allow air to be drawn into or expelled through the tube to equalize pressure in the gastrointestinal tract during these operations. Connection to the main lumen is typically completed by inserting a catheter tip syringe or similar structure into the proximate end of the main lumen. For example, where a source of nutrition is connected to the main lumen the connection may be made using any of a variety of connection hardware. Because a single approach is not used, the hardware selection must be made by users on an ad hoc basis.

The recent adoption of ISO/IEC DIS 80369-3 provides a uniform standard for small bore connectors for enteral applications. However, these standards do not provide a standardized connection suitable for use with the most common types of nasogastric tubing.

Different adapters could be used depending on whether a connection is being made to a feeding device or a suction device. But such an approach can lead to confusion over the choice of adapter for a given situation. Thus, it is a poor solution when a goal of the ISO standard is improved patient safety through standardization.

Further, loose connectors can also be lost or misapplied because they can be freely separated from the enteral feeding tube and any associated device. Current approaches to tether loose devices are also deficient because their flexibility can make them more difficult to use in certain applications. Further, they are manufactured from material that is easily cut or removed from the connector.

Accordingly, it would be advantageous to provide a connector for fluidly coupling to the main lumen of medical tubing that is also removable from the main lumen. Further, it would be advantageous to provide such a connector that meets the current standards for enteral applications and is suitable for use with medical tubes included in the most common nasogastric tube assemblies. Further, it would be advantageous to provide the preceding with hardware that allows the connector to be secured so that it is not misplaced from the medical tubing.

SUMMARY

According to various aspects, an adapter provides a fluid-tight connection between some of the most common types of nasogastric tubes and a medical device that employs a connector that meets the ISO/IEC DIS 80369-3 standard. In particular, various embodiments provide a fitting configured to receive a female connector that meets the above ISO standard for small bore connectors for enteral applications. In these embodiments, the fitting receives the female connector in a fluid-tight manner while also providing a fluid-tight connection to the main lumen of a nasogastric tube.

According to one aspect, a connector system is configured to fluidly connect a nasogastric tube assembly including a lumen and a tube to a medical device. The system includes a connector including: a fitting configured to provide a fluid-tight connection with the medical device; a neck coupled to the fitting, the neck configured to attach to the nasogastric tube assembly; and a body coupled to the neck, the body configured to provide a fluid-tight connection with the nasogastric tube assembly when at least partially inserted within the lumen; and a first tether including a first fastening region defining a first opening configured to receive the neck, a second fastening region defining a second opening configured to couple to the nasogastric tube assembly, and a link coupling the first fastening region to the second fastening region, the link configured to maintain a fixed distance separating the first fastening region from the second fastening region.

In one embodiment, the connector system includes a cap configured to seal the fitting where the cap includes a knob and a plug coupled to the knob, the plug including at least one thread sized and configured to complete a fluid-tight threaded attachment of the cap to the fitting.

In another embodiment, the second fastening region defines a second opening, and the first tether includes a resilient arm moveable between a latched position that secures the tube included in the nasogastric tube assembly within the second opening and an unlatched position that permits the tube included in the nasogastric assembly to be removed from the second opening.

According to another aspect, a kit includes a nasogastric tube assembly including a main lumen, a vent lumen and tubing fluidly coupled to the vent lumen; a rigid tether configured to secure to the tubing and a connector. In one embodiment, the connector includes: a fitting including a longitudinal axis, an annular collar having an inside surface and an outside surface, the fitting including a threaded region located on the inside surface and configured to complete a fluid-tight connection with a medical device; a fastening region coupled to the fitting, the fastening region configured to securely attach to the rigid tether, the fastening region including an outside diameter sized and configured to allow the connector to freely rotate about the longitudinal axis with the fastening region securely attached to the rigid tether; and a body coupled to the fastening region, the body configured to provide a fluid-tight connection with the nasogastric tube assembly when at least partially inserted within the main lumen.

According to still another aspect, a method of connecting a medical device to a nasogastric tube assembly in a fluid-tight manner is provided where the nasogastric tube assembly includes a main lumen, a vent lumen and anti-reflux valve tubing. According to one embodiment, the method includes providing a connector system including a connector having: a fitting configured to provide a fluid-tight connection with the medical device; a neck coupled to the fitting, the neck configured to attach to the nasogastric tube assembly; and a body coupled to the neck, the body configured to provide a fluid-tight connection with the nasogastric tube assembly when at least partially inserted within the lumen; and a first tether including a first fastening region defining a first opening configured to receive the neck, a second fastening region defining a second opening configured to couple to the nasogastric tube assembly, and a link coupling the first fastening region to the second fastening region, the link configured to maintain a fixed distance separating the first fastening region from the second fastening region. According to this embodiment, the neck is securely received within the first fastening region of the first tether and the method includes inserting the body within the main lumen; securing the anti-reflux valve tubing within the second opening at a point of attachment to maintain the neck at the fixed distance relative to the point of attachment; holding the connector by the fitting to control a rotational position of the connector; and changing the relative rotational position of at least one of the connector and a connector included with the medical device relative to one another to complete a fluid-tight threaded connection.

According to a further aspect, a method of assembling an adapter kit is provided. In one embodiment, the method includes providing an adapter configured to complete a fluid-tight connection between a medical device and a medical tube including a main lumen and a secondary lumen, the adapter including a fitting with a collar having a first outside diameter, a body and a neck connecting the fitting to the body, the neck sized and configured with a second outside diameter smaller than the first outside diameter, the body configured to provide a fluid tight connection to the main lumen when at least partially inserted therein; and attaching a rigid tether around the neck, the rigid tether including a resilient arm configured to secure the adapter to tubing included in the medical tube in a removable manner and to locate the adapter a fixed distance from the tubing when the rigid tether is attached to the tubing, wherein the rigid tether is configured to allow the adapter to rotate 360° about the longitudinal axis of the adapter when adapter is secured to the tubing by the rigid tether.

According to one embodiment, the method includes providing a cap including a plug, a knob and a neck region connecting the plug to the knob, the plug configured to form a fluid tight connection with the fitting via a threaded connection to the fitting. In a further embodiment, the method includes coupling the cap to the adapter via a flexible tether having a first end and a second end, the first end being secured around the neck of the adapter, the second end being secured around the neck region of the cap, wherein the cap is free to rotate 360° about a longitudinal axis of the cap when secured to the tether, and wherein the adapter is free to rotate 360° about a longitudinal axis of the adapter when attached to the tether According to a still further embodiment, a connector is configured to fluidly connect a nasogastric tube assembly including a lumen and a tube to a medical device. The a connector includes a fitting configured to provide a fluid-tight connection with the medical device; a neck coupled to the fitting, the neck configured to attach to the nasogastric tube assembly; and a body coupled to the neck, the body configured to provide a fluid-tight connection with the nasogastric tube assembly when at least partially inserted within the lumen, and without the aid of any additional hardware to complete the fluid tight connection with the nasogastric tube assembly.

As used herein, the term "fluid" refers to a gas or a liquid. One of ordinary skill in the art will recognize that fluids can include water, medication, nutrition or other administrative fluids. According to some embodiments, the fluid includes a contrast, for example a radiological contrast.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
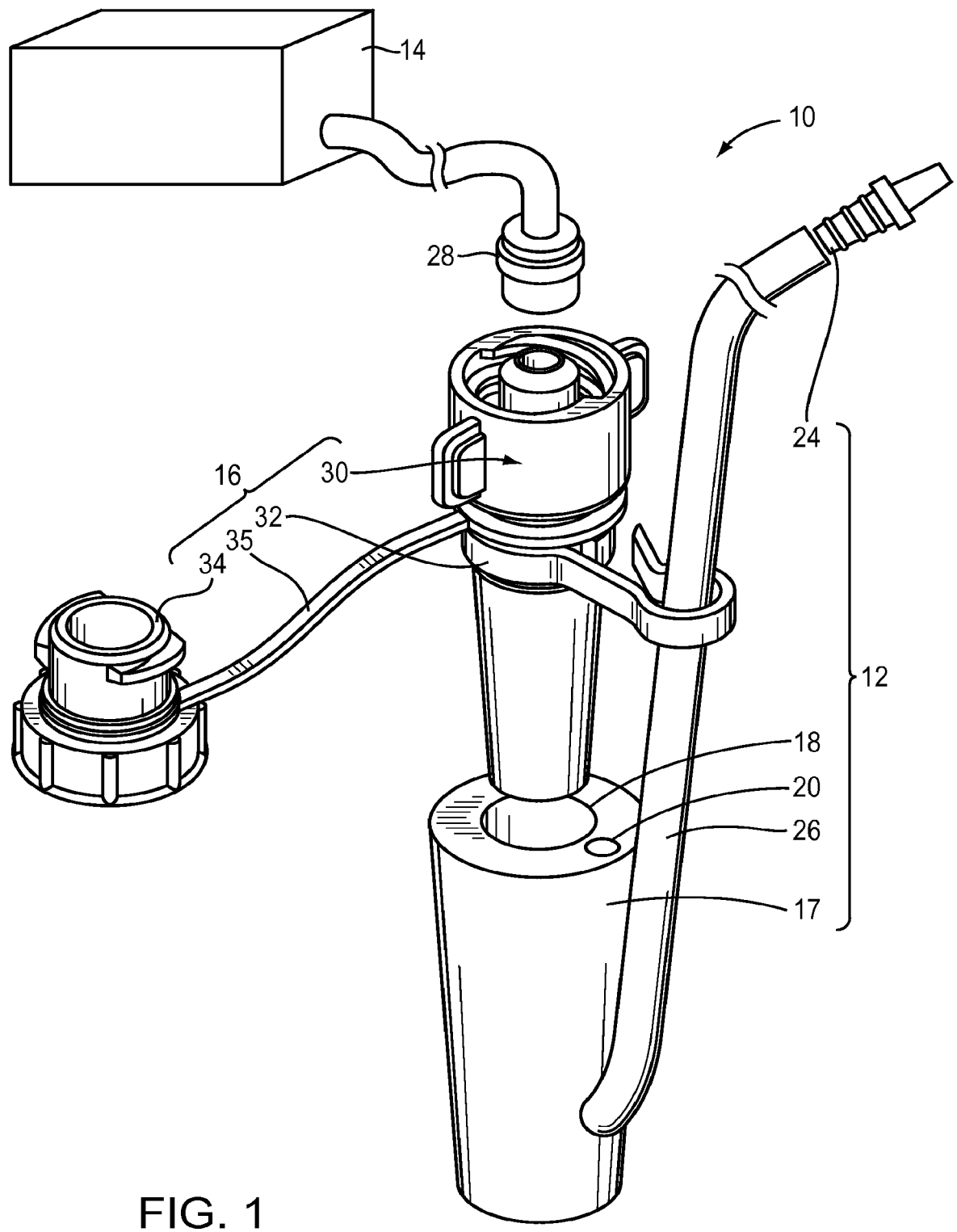
FIG. 1 is a perspective view of the presently disclosed enteral system in accordance with one or more aspects.

FIG. 1 illustrates an embodiment of the presently disclosed enteral system 10. The enteral system 10 includes an enteral tube system 12, a medical device 14, and a connector system 16. The enteral tube system 12 can assume a variety of configurations depending on the embodiment. In the illustrated embodiment, the enteral tube system 12 includes a medical tube 17 including a main lumen 18, a vent lumen 20, an anti-reflux valve (ARV) 24 and anti-reflux valve tubing 26. As will be recognized by those of ordinary skill in the art, various embodiments of the connector system 16 can be employed with the medical tube 17 provided in other configurations. For example, in one embodiment, the medical tube 17 includes the main lumen 18 and the vent lumen 20 but does not include any form of tubing extension such as the anti-reflux valve tubing 26. In another example, the medical tube 17 includes only the main lumen 18. Further, in some embodiments, the enteral tube system includes a tubing extension such as the anti-reflux valve tubing 26 but does not include the anti-reflux valve 24.

According to the illustrated embodiment, the connector system 16 includes a connector 30, a first tether 32 and a cap 34 where the cap 34 is attached to the connector 30 by a second tether 35. The cap 34 is configured to attach to a proximate end of the connector 30 in a fluid-tight manner, for example, using a threaded attachment. The first tether 32 is configured to attach the connector 30 to a portion of the enteral tube system 12. In the illustrated embodiment, the first tether 32 secures the connector 30 to the anti-reflux valve tubing 26. Further, the first tether 32 can be configured to releasably secure the connector 30 to the enteral tube system 12 at a point of attachment. The preceding allows the connector system 16 to be replaced while preventing the system 16 from being misplaced from the enteral tube system 12 during use. According to these embodiments, the point of attachment is a location at which the tether is secured to medical tubing.

In various embodiments, the medical device 14 includes a fitting 28 configured to secure to the connector system 16 in a fluid-tight manner. Depending on the embodiment, the medical device 14 can assume a variety of configurations. For example, the medical device 14 can include a feeding system that provides nutrition to a patient where the medical device is in the form of any of a pumps, gravity systems such as a tube bag, or a syringe and/or syringe pump. Further, the medical device 14 is not limited to use in providing nutrition but can be a source of suction, of administrative fluid (including nutritional fluid) and/or contrast, as some examples. These embodiments can also be provided in the form of feed pump, a gravity feed system such as a feeding tube bag, or a syringe and/or syringe pump. According to each of the preceding embodiments, the fitting 28 is configured to secure to the connector system 16 in a fluid-tight manner.

Figures 2A, 2B:
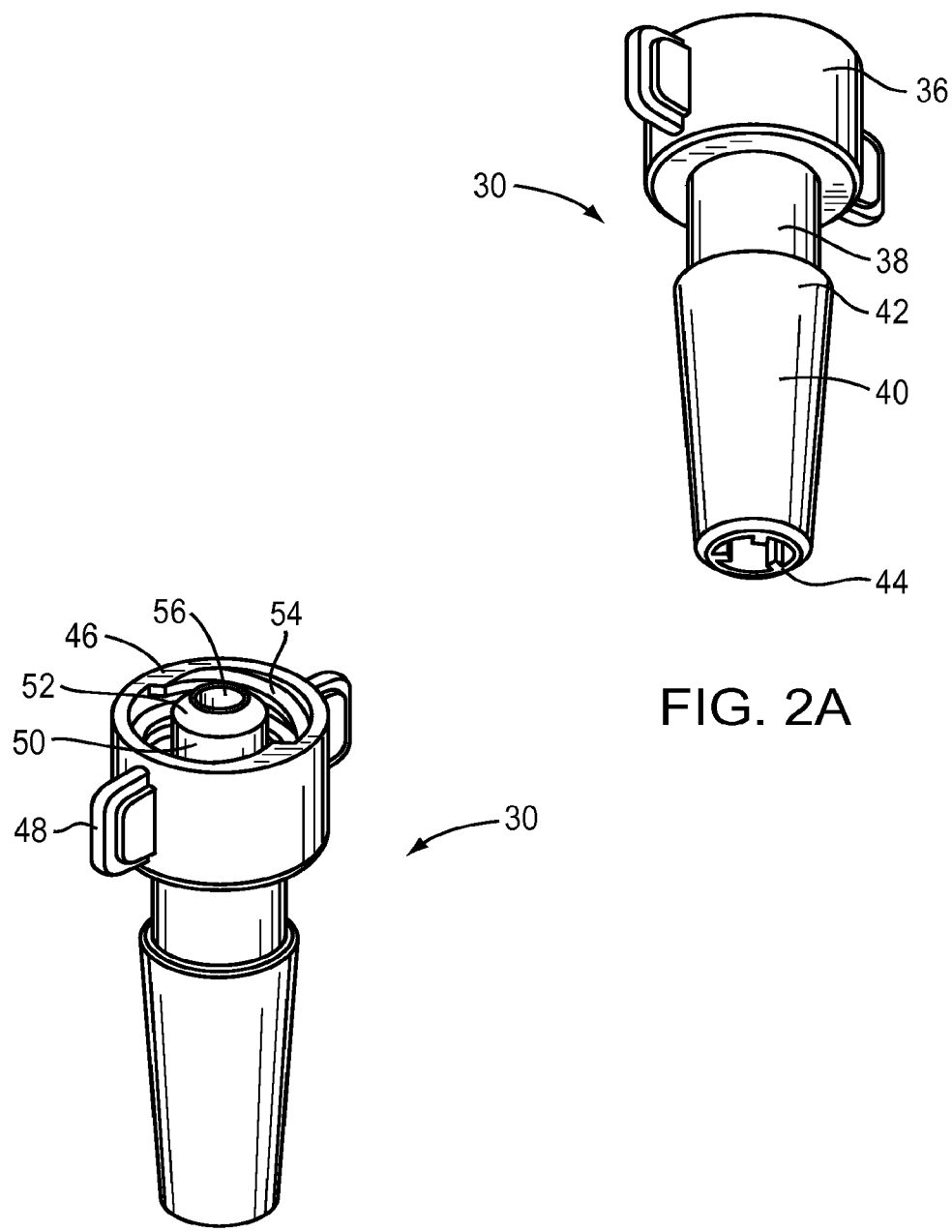
FIG. 2A is a perspective view of a connector of the enteral system illustrated in FIG. 1.
FIG. 2B is an alternate perspective view of the connector of the enteral system illustrated in FIG. 1.

FIGS. 2A and 2B illustrate the connector 30 according to an embodiment in which the connector 30 includes a fitting 36, a neck 38 and a body 40. Further, the body 40 includes a first end 42 attached to the neck 38 and a second end 44 where the second end provides a distal end of the connector 30.

As illustrated in FIG. 1, the first tether 32 and the second tether 35 are secured around the neck 38. In some embodiments, the neck 38 has an outside diameter that is smaller than the outside diameter of the fitting 36. According to one embodiment, the outside diameter of the neck 38 is no more than 0.25 inches smaller than the outside diameter of the fitting 36. Further, the outside diameter of the neck 38 can also be smaller than the outside diameter of the first end 42 of the body 40. These embodiments are well suited where either or both of the first tether 32 and the second tether 35 are employed because they can limit the longitudinal movement of the first tether 32 and the second tether 35 when secured around the neck 38.

As illustrated in FIG. 2A, the body 40 provides a taper because the outside diameter of the body narrows from a maximum diameter at the first end 42 to a minimum diameter at the second end 44. In various embodiments, the body 40 is suitable for insertion in the main lumen 18 in a fluid-tight manner using only a friction fit that does not require any external hardware such as clamps, etc. To improve the sealing properties of the body, the outside surface of the body 40 should be free from any defects or manufacturing artifacts. For example, in embodiments in which the connector 30 is manufactured in an injection molding process, the outside surface of the body 40 should be free of any sink marks or parting lines. As described herein, the body 40 can be provided in other configurations depending on the embodiment.

FIG. 2B illustrates further details of the connector 30 including a collar 46 included as a part of the fitting 36. In the illustrated embodiment, tabs 48 extend radially outward from the collar 46 at locations spaced 180° apart from one another. A male fluid conduit 50 is located within the fitting 36 and includes a tapered tip 52. In the illustrated embodiment, the tapered tip 52 extends outside a region defined by the collar 46 and provides a proximate end of the connector 30. According to one embodiment, the collar has an outside diameter of between 12.0 mm and 12.3 mm.

According to various embodiments, the collar 46 includes a set of threads 54 located on an inside surface. In one embodiment, the collar 46, the fluid conduit 50 and the set of threads 54 are configured to receive a female fitting with threads suitable for attachment to the threads 54. Further, the connector 30 includes a fluid path 56 that runs from the tapered tip 52 to the second end 44 of the body 40.

According to a further embodiment, the fitting 28 included with the medical device 14 is a female fitting including threads and other structure suitable to secure to the connector 30 in a fluid-tight manner such that the medical device 14 is fluidly coupled to the to the fluid path provided by the connector 30.

According to some embodiments, the set of threads 54 conform to ISO/IEC DIS 80369-3. Further, in some embodiments, the tapered tip 52 includes a taper that conforms to ISO/IEC DIS 80369-3.

Figure 3A:
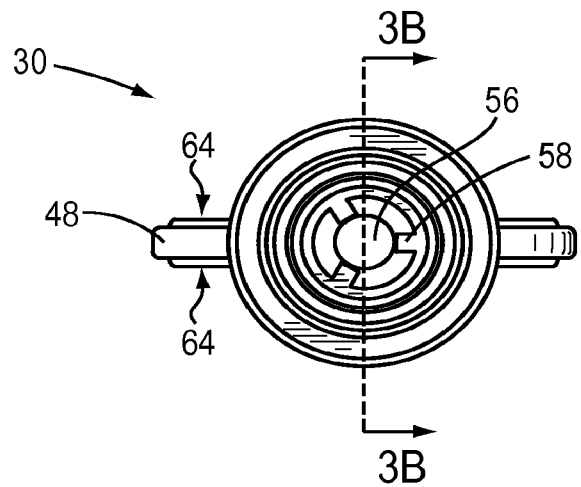
FIG. 3A is a bottom plan view of the connector of the enteral system illustrated in FIG. 1.
Figure 3B:
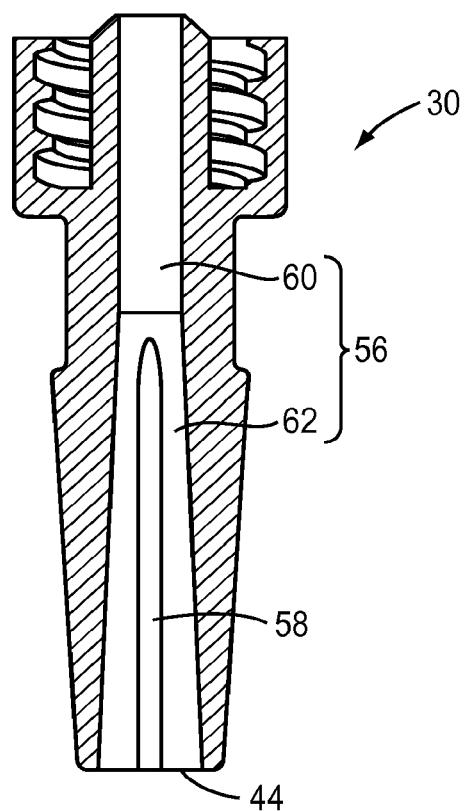
FIG. 3B is a cross sectional view of the connector of the enteral system illustrated in FIG. 1.

FIGS. 3A and 3B illustrate an embodiment of the connector 30 in which an inside wall of the fluid path 56 includes a set of projections 58, for example, ribs. The cross-sectional view provided by FIG. 3B further illustrates that the fluid path 56 includes a first region 60 and a second region 62. In the illustrated embodiment, the first region 60 has a constant diameter while the second region 62 includes a tapered cross section that widens in diameter from a connection to the first region 60 until it reaches the second end of the body 44. According to these embodiments, the diameter of the first region 60 conforms to ISO/IEC DIS 80369-3 while the diameter provided at the second end of the body 44 more closely matches the outside diameter of the main lumen 18. Thus, the change in diameter of the fluid path 56 can provide a transition between a diameter of the fluid path provided by the medical equipment 14 and a diameter of the fluid path provided by the main lumen 18. The ribs 58 can be included to provide support in the second region 62 where the walls of the body become thinner.

Referring again to FIG. 3A, each tab 48 includes a planar surface 64 provided on opposite sides of the tab 48. The tabs 48 are configured to allow a user to more easily grasp the fitting 36 when handling the connector 30. For example, the tabs 48 are configured to allow a user to more easily control a rotational position of the connector. The preceding is particularly advantageous where a threaded connection is employed to attach to the medical device 14 because the threaded connection necessarily requires that a rotational position of the connector 30 and the fitting 28 be changed relative to one another. According to one embodiment, a rotation of less than ½ turn is all that is required to complete a fluid-tight connection between the fitting 36 and the fitting 28. Further, the preceding can be achieved without use of a gasket, o-ring or other sealing element in accordance with various embodiments. According to various embodiments, the connector 30 is manufactured from, for example, a molded plastic such as ABS or PVC.

Figure 4A:
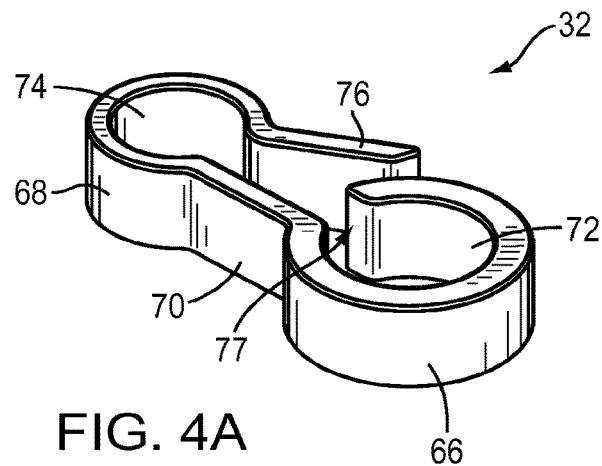
FIG. 4A is a perspective view of a tether of the enteral system illustrated in FIG. 1.
Figure 4B:
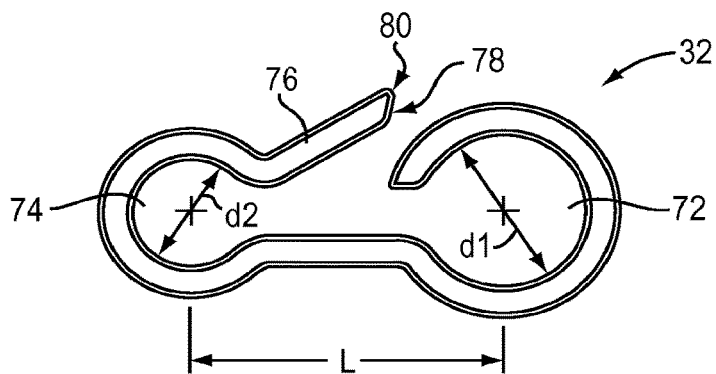
FIG. 4B is a plan view of the tether of the enteral system illustrated in FIG. 1 in an unlatched state.

Referring now to FIGS. 4A and 4B, the first tether 32 is illustrated in accordance with some embodiments. The first tether 32 includes a first fastening region 66 and a second fastening region 68 connected to one another by a link 70. According to this embodiment, the first fastening region 66 defines a first opening 72 and the second fastening region 68 defines a second opening 74. In addition, the first tether 32 includes a resilient arm 76 extending from a free end of the second fastening region 74. In the illustrated embodiment, the first region includes a surface 77 located at a free end of the first fastening region 66.

Referring to FIG. 4B, the first opening 72 has a diameter d1 and the second opening 74 has a diameter d2. The link 70 has a length that fixes a distance separating the first opening 72 and the second opening 74 to a distance L. According to the illustrated embodiment, the first fastening region 66 is sized and configured to provide a first opening 72 to receive the neck 38 of the connector 30 and the second fastening region 68 is sized and configured to provide a second opening 74 to receive tubing included in the enteral tube system 12. In various embodiments, the first region 66 of the first tether 32 is attached to the connector 30 at the neck 38 in advance of the connector being shipped by the manufacturer. According to a further embodiment, an enteral kit includes the connector 30 attached to an element of the enteral tube system 12 by the first tether 32.

A problem identified in prior approaches is the ease with which tethers in general can be defeated by, for example, cutting. Further, flexible tethers can allow the elements connected by the tether to change a distance of separation from one another. Accordingly, in some embodiments, the first tether 32 is manufactured with dimensions and material to provide a rigid structure, for example, a structure that maintains the fixed distance between the first fastening region 66 and the second fastening region 68. As a result, the the first opening 72 from the second opening 74 are also separated by a fixed distance. In some embodiments, the distance L is a predetermined distance selected based on the diameter of the tubing to which the tether is attached and/or the diameter of the fitting 36. For example, the link 70 can provide a rigid arm to achieve the preceding. According to various embodiments, the preceding is provided where the first tether 32 is manufactured, for example, from a molded plastic such as ABS or PVC with dimensions to provide a rigid structure. For example, a thickness of the first tether and a length of the link 70 can be selected to provide a rigid construction.

Figure 4C:
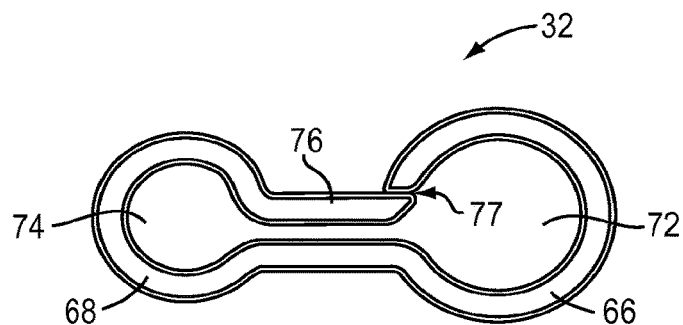
FIG. 4C is a plan view of the tether of the enteral system illustrated in FIG. 1 in a latched state.

Referring to FIG. 4C, the first tether 32 is illustrated in a closed position with a distal end of the resilient arm 76 secured in place by engagement with the surface 77 provided by the first fastening region 66. FIG. 4B illustrates a first surface 78 and a second surface 80 provided at a distal end of the resilient arm 76. According to this embodiment, the first surface 78 and the second surface 80 provide respective angled surfaces that allow the resilient arm 76 to more easily slide into and out of engagement with the surface 77 as the tether is latched and unlatched.

The resilient arm 76 travels in a generally arcuate path between the open position (or unlatched position) illustrated in FIG. 4B and the closed (or latched position) illustrated in FIG. 4C. For example, to move the resilient arm 76 from the open to closed position, the distal end of the arm 76 is moved toward the first fastening region 66, contact between the first surface 78 and the free end of the first fastening region 66 forces a slight compression of the second fastening region 74 (which can slightly reduce the diameter d2), the second surface 80 slides beneath the surface 77, the compression of the second fastening region is released and the outer surface of the resilient arm 76 slides beneath the surface 77 when the second fastening region returns to its uncompressed state. To move the flexible arm from the closed to the open position, the distal end of the arm 76 is moved in the direction of the second fastening region 68 by applying pressure to the second fastening region (again, slightly reducing the diameter d2), the outer surface of the resilient arm 76 slides beneath the surface 77 as the second fastening region 74 is compressed, the second surface 80 slides beneath the surface 77, the distal end of the resilient arm 76 travels far enough to release the resilient arm 76 from engagement with the surface 77 and the second fastening region returns to its uncompressed state with the resilient arm located as illustrated in FIG. 4B.

Figure 5A:
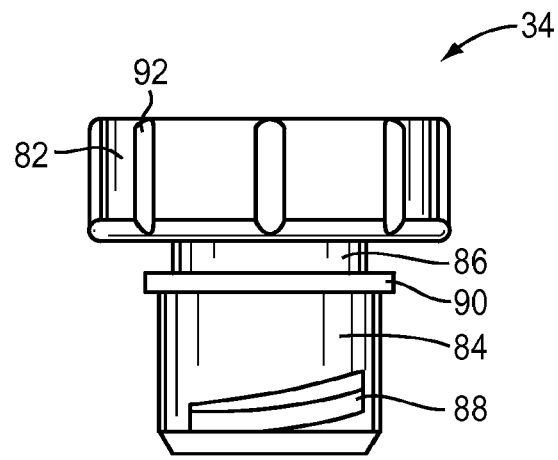
FIG. 5A is a plan view of the cap of the enteral system illustrated in FIG. 1.

Referring to FIG. 5A, the cap 34 is illustrated in an embodiment in which it includes a knob 82 and a plug 84. According to a further embodiment, the cap 34 also includes a neck 86 and at least one thread 88 configured to engage the threaded region 54 located on the inside of the collar 46. In various embodiments, the at least one thread 88 includes a plurality of threads. Further, the cap can include a flange 90 located at a junction of the plug 84 and the neck 86.

The cap 34 can include the second tether 35, as illustrated in FIG. 1, to keep the cap 34 attached to the connector 30 when the plug 84 is unthreaded from the fitting 36. According to one embodiment, a first end of the flexible tether 35 is secured to the cap 34 in the region of the neck 86, for example, with a loop secured 360° about the neck 86. Further to this embodiment, axial movement of the loop is restricted to the region located between the knob 82 and the flange 90. According to this embodiment, a second loop located at the second end of the flexible tether is secured to the connector 30, for example, in the region of the neck 38. Further, the second loop can be secured 360° about connector 30 at a region of the neck 38 located between the fitting 36 and the first tether 32. FIG. 1 illustrates one such embodiment where the second tether 35 includes a central strip that is attached to loops located around each of the neck 38 and the neck 86.

According to a further embodiment, the knob 82 includes a plurality of projections 92 located about an annular surface of the knob. In this embodiment, the projections 92 include a linear shape and project in a substantially radial direction. According to this embodiment, the projections 92 provide structure that allows a user to grasp the cap 34 more securely to when it is threaded to or unthreaded from the fitting 36 included in the connector 30.

Figure 5B:
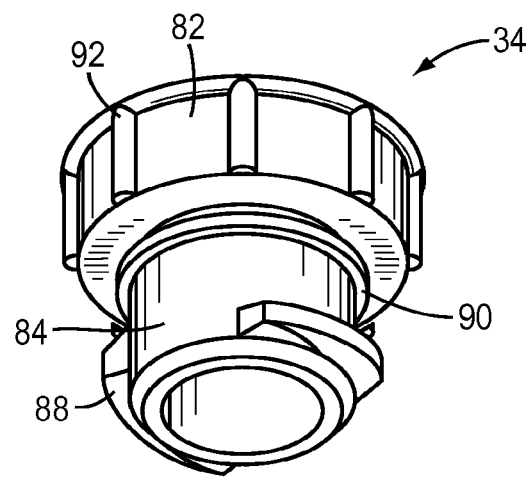
FIG. 5B is a perspective view of a cap of the enteral system illustrated in FIG. 1.

FIG. 5B shows the cap 34 in a perspective view that illustrates the pair of threads 88. According to some embodiments, the shape and dimensions of the plug 84 and the threads 88 conform to ISO/IEC DIS 80369-3. In these embodiments, a rotation of less than ½ turn is all that is required to complete a fluid-tight connection between the cap 34 and the fitting 36.

Figure 6A:
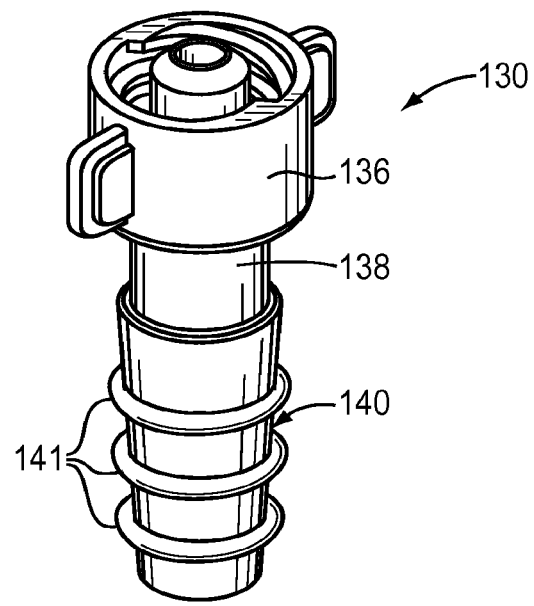
FIG. 6A is a perspective view of a connector in accordance with another embodiment.
Figure 6B:
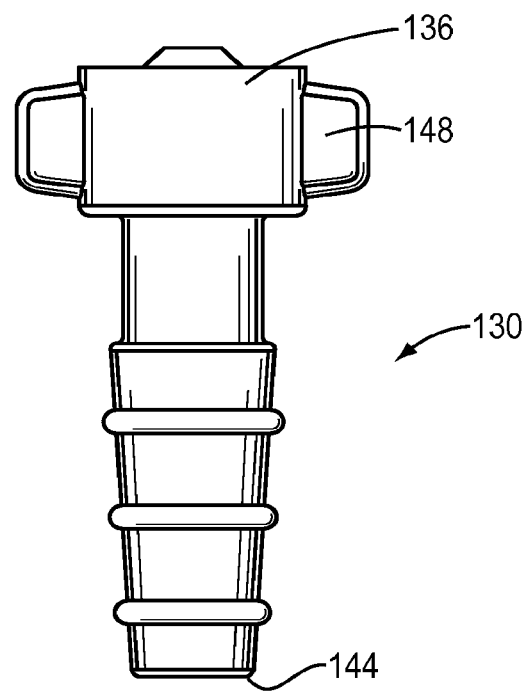
FIG. 6B is a plan view of the connector illustrated in FIG. 6A.

FIGS. 6A and 6B illustrate a connector 130 in accordance with another embodiment. According to this embodiment, the connector 130 includes a fitting 136, a neck 138 and a body 140. However, in this embodiment, the body 140 includes one or more projections 141. As a result, the body 140 provides a barbed structure to assist in securing the body in place in a fluid-tight manner when inserted within the main lumen 18. To assist a user in gripping the connector 130 the fitting 136 can include one or more tabs 148 or "wings."

According to various alternate embodiments, the body 30, 130 can include a variety of structure with which to engage the main lumen. For example, in one embodiment, the body includes a series of tapered steps gradually decreasing in diameter with the widest diameter step located nearest the neck 38, 138 and the smallest diameter step located nearest the second end 44, 144 of the body 30, 130, respectively.

According to some embodiments, the connector 30, 130 and the first tether 32 can be included in a kit along with the nasogastric tube assembly, or alternatively, a different type of medical tube with which the connector 30, 130 is used. According to these embodiments, the first tether 32 is secured around the neck 38, 138 of the connector when assembled for inclusion in the kit. In further embodiments, the first tether is also attached to the medical tubing. Here, the kit facilitates an easy application of the connector for the end user in a manner that also assists in maintaining the association of the connector 30, 130 with the medical tubing. In some embodiments, the body 40, 140 of the connector 30, 130 is also inserted in medical tubing when the kit is assembled.

Embodiments of the kit can also include the cap 34. In some of these embodiments, the kit includes the second tether 35 secured to both the cap 34 and the connector 30. According to these embodiments, a kit includes each of the enteral tube system 12 (or other medical tubing) and the connector system 16 illustrated in FIG. 1. According to the various embodiments that provide a kit, all the elements of the kit can be located in a single product package, for example, packaged together in a sealed package that includes a stomach tube including a dual lumen with anti-reflux valve. In one embodiment, the preceding is packaged together in a sealed package along with the connector 30, 130, the first and second tethers 32, 35, respectively, and the cap 34.

Although primarily described with reference to a naso-gastric tube, gastro-intestinal access can also be achieved via insertion of a tube through an incision in the patient. Embodiments of the connector, connector system and kits described herein can be employed with these and other forms of enteral tubing. Further, the embodiments described herein are not limited to use with any one type of medical tube and can instead be employed with a variety of types of medical tubing that employ a fitting to complete a fluid-tight engagement with the medical tube. Various embodiments described herein can be employed with suction only medical devices, oral only medical devices, skin level gastrostomy medical devices, enteral feeding reservoirs and other health-care applications.

In some embodiments, the connector 30 and the tether 32 are manufactured from a rigid plastic material. In other embodiments, the tether 32 is manufactured from a semi-rigid material. According to these embodiments, a rigidity of the link 70 is sufficient to maintain a fixed distance between the first fastening region 66 and the second fastening region 68. Various embodiments including those manufactured by an injection molding process can be manufactured from a corrosion resistance material with a smooth surface. In one embodiment, the roughness value Ra shall not exceed 0.8 micrometers on outer surfaces. Further, the connector 30 can be manufactured from material compatible with drugs with which it is intended to be used.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A connector system configured to fluidly connect a nasogastric tube assembly including a main tube and a tube extension to a medical device, the system comprising:
   a connector including:
      a fitting configured to provide a fluid-tight connection with the medical device;
      a neck coupled to the fitting, the neck configured to attach to the nasogastric tube assembly; and
      a body coupled to the neck, the body configured to provide a fluid-tight connection with the nasogastric tube assembly when at least partially inserted within the main tube;
   a first tether including a first fastening region defining a first opening receiving the neck, and a second fastening region configured to couple to the naso-gastric tube assembly;
   a cap configured to seal the fitting; and
   a second tether including a first fastening region received around the neck of the connector, and a second fastening region attached to the cap to couple the cap to the neck of the connector,
   wherein the first fastening region of the first tether is defined by a continuous first semi-circular segment extending along an arc through an angle of greater than 180° in all operating positions,
   wherein the second fastening region of the first tether is defined by a continuous second semi-circular segment extending along an arc through an angle of greater than 180° in all operating positions, and
   wherein the first tether is configured to form an enclosed shape comprising the first fastening region of the first tether, the second fastening region of the first tether, and a linear section therebetween.

2. The connector system of claim 1, wherein the second tether is more flexible than the first tether.

3. The connector system of claim 1, wherein the cap includes a knob and a plug coupled to the knob, the plug including at least one thread sized and configured to complete a fluid-tight threaded attachment of the cap to the fitting.

4. The connector system of claim 3, wherein the knob includes an annular surface having raised regions.

5. The connector system of claim 1, wherein the neck has a first length and the body has a second length, the first length being less than the second length.

6. A kit comprising:
   a connector including:
      a fitting including a longitudinal axis, an annular collar having an inside surface and an outside surface, the fitting including a threaded region located on the inside surface and configured to complete a fluid-tight connection with a medical device;
      a fastening region coupled to the fitting, the fastening region including a neck; and
      a body coupled to the fastening region, the body configured to provide a fluid-tight connection with a nasogastric tube assembly when at least partially inserted within the nasogastric tube assembly; and
   a rigid tether secured around the neck of the fastening region of the connector,
      wherein the rigid tether comprises a first fastening region and a second fastening region spaced from the first fastening region by a linear section having a first length, the neck being received in the first fastening region,
      wherein the first fastening region is defined by a continuous first semi-circular segment extending along an arc through an angle of greater than 180° in all operating positions and the second fastening region is defined by a continuous second semi-circular segment extending along an arc through an angle of greater than 180° in all operating positions, and wherein the rigid tether is configured to form an enclosed shape comprising the first fastening region, the second fastening region, and the linear section; the kit including the connector and the rigid tether being located in a single sealed product package.

7. The kit of claim 6, further comprising a nasogastric tube assembly comprising medical tubing including a main lumen and a vent lumen, and a tube extension attached to the medical tubing and fluidly coupled to the vent lumen, the nasogastric tube assembly being located in the single sealed product package.

8. The kit of claim 7, wherein the tube extension of the nasogastric tube assembly is received in the second fastening region securing the tube extension to the connector in the single sealed product package.

9. The kit of claim 8, wherein the body is received in the main lumen of the medical tubing securing the connector to the medical tubing in the single sealed product package.

10. The kit of claim 6, further comprising a cap including a knob and a plug coupled to the knob, the plug including at least one thread sized and configured to complete a fluid-tight threaded attachment of the cap to the fitting.

11. A method of assembling an adapter kit, the method comprising:
providing an adapter configured to complete a fluid-tight connection between a medical device and medical tubing including a main tube and a tube extension,
the adapter including a fitting with a collar having a first outside diameter, a body, and a neck connecting the fitting to the body,
the neck sized and configured with a second outside diameter smaller than the first outside diameter,
the body configured to provide a fluid tight connection to the medical tubing when at least partially inserted therein, and
the fitting including a threaded region located on an inside surface thereof and configured to provide a fluid-tight connection with the medical device;
attaching a rigid tether around the neck of the adapter,
wherein the rigid tether comprises a first fastening region and a second fastening region spaced from the first fastening region by a linear section having a first length, the neck being received in the first fastening region,
wherein the first fastening region is defined by a continuous first semi-circular segment extending along an arc through an angle of greater than 180° in all operating positions and the second fastening region is defined by a continuous second semi-circular segment extending along an arc through an angle of greater than 180° in all operating positions, and
wherein the rigid tether is configured to form an enclosed shape comprising the first fastening region, the second fastening region, and the linear section; and
packaging the adapter and rigid tether in a single sealed product package.

12. The method of claim 11, further comprising receiving the tube extension of the medical tubing in the second fastening region prior to packaging the adapter and rigid tether in the single sealed product package.

13. The method of claim 12, further comprising inserting the body of the adapter in the main tube of the medical tubing prior to packaging the adapter and rigid tether in the single sealed product package.

14. The method of claim 11, further comprising providing a cap including a plug, a knob, and a neck region connecting the plug to the knob, the plug configured to form a fluid tight connection with the fitting via a threaded connection connectable to the threaded region of the fitting.

15. A connector system configured to fluidly connect a nasogastric tube assembly including a main tube and a tube extension to a medical device, the system comprising:
a connector including:
a fitting configured to provide a fluid-tight connection with the medical device; a neck coupled to the fitting, the neck configured to attach to the nasogastric tube assembly; and
a body coupled to the neck, the body configured to provide a fluid-tight connection with the nasogastric tube assembly when at least partially inserted within the lumen; and
a rigid tether configured to secure to the nasogastric tube assembly, the rigid tether comprising a first fastening region defined by a continuous first semi-circular segment extending along an arc through an angle of greater than 180° in all operating positions, a link extending from an end of the first fastening region and defined by a first linear segment and a second linear segment, a second fastening region defined by a continuous second semi-circular segment extending along an arc through an angle of greater than 180° in all operating positions and extending from an end of the link,
wherein the rigid tether is configured to form an enclosed shape comprising the first fastening region, the second fastening region, the first linear segment, and the second linear segment.

* * * * *